United States Patent
Ishikawa et al.

(10) Patent No.: US 10,526,288 B2
(45) Date of Patent: Jan. 7, 2020

(54) METHOD FOR PREPARING 4-(PIPERIDIN-4-YL)MORPHOLINE

(71) Applicant: YUKI GOSEI KOGYO CO., LTD., Tokyo (JP)

(72) Inventors: Hiromi Ishikawa, Tokyo (JP); Kiyono Nakagawa, Tokyo (JP); Yukiko Takeda, Tokyo (JP)

(73) Assignee: YUKI GOSEI KOGYO CO., LTD., Tokyo (JP)

( * ) Notice: Subject to any disclaimer, the term of this patent is extended or adjusted under 35 U.S.C. 154(b) by 0 days.

(21) Appl. No.: 16/308,312

(22) PCT Filed: Jun. 9, 2017

(86) PCT No.: PCT/JP2017/021419
§ 371 (c)(1),
(2) Date: Dec. 7, 2018

(87) PCT Pub. No.: WO2017/213245
PCT Pub. Date: Dec. 14, 2017

(65) Prior Publication Data
US 2019/0210968 A1    Jul. 11, 2019

(30) Foreign Application Priority Data
Jun. 9, 2016 (JP) .................. 2016-115040

(51) Int. Cl.
| | | |
|---|---|---|
| C07D 211/72 | (2006.01) | |
| C07D 265/30 | (2006.01) | |
| C07D 413/04 | (2006.01) | |
| C07D 211/58 | (2006.01) | |
| C07B 61/00 | (2006.01) | |

(52) U.S. Cl.
CPC ............ *C07D 211/58* (2013.01); *C07B 61/00* (2013.01)

(58) Field of Classification Search
CPC ... C07D 211/72; C07D 265/30; C07D 413/04
See application file for complete search history.

(56) References Cited

U.S. PATENT DOCUMENTS

| | | |
|---|---|---|
| 7,696,346 B2 | 4/2010 | Huchler et al. |
| 8,288,531 B2 | 10/2012 | Schnaubelt et al. |
| 2008/0045705 A1 | 2/2008 | Huchler et al. |
| 2010/0152439 A1 | 6/2010 | Huchler et al. |
| 2011/0087021 A1 | 4/2011 | Schnaubelt et al. |
| 2011/0295000 A1 | 12/2011 | Huchler et al. |

FOREIGN PATENT DOCUMENTS

| | | |
|---|---|---|
| CN | 105777615 A | 7/2016 |
| JP | 63141963 A | 6/1988 |
| JP | 7116145 B2 | 12/1995 |
| JP | 7116146 B2 | 12/1995 |
| JP | 11222431 A | 8/1999 |
| JP | 2010501517 A | 1/2010 |
| JP | 2010535838 A | 11/2010 |

OTHER PUBLICATIONS

International Search Report issued in PCT/JP2017/021419, dated Jul. 4, 2017.

*Primary Examiner* — Brenda L Coleman
(74) *Attorney, Agent, or Firm* — Heslin Rothenberg Farley & Mesiti P.C.

(57) ABSTRACT

The object of the present invention is to provide a method for preparing 4-(piperidin-4-yl)morpholine, which is easy to operate. The object can be solved by a method for preparing 4-(1-benzylpiperidin-4-yl)morpholine, characterized in that 5-fold molar or more of morpholine is added to 1-benzyl-4-piperidone, and the mixture is reacted with hydrogen under 1 MPa or less in the presence of platinum catalyst or palladium catalyst.

9 Claims, No Drawings

METHOD FOR PREPARING 4-(PIPERIDIN-4-YL)MORPHOLINE

CROSS REFERENCE TO RELATED APPLICATIONS

This application is a U.S. National Phase filing under 35 U.S.C. § 371 of International Application PCT/JP2017/021419, filed Jun. 9, 2017, and published as WO 2017/213245 A1 on Dec. 14, 2017. PCT/JP2017/021419 claims priority of Japanese Patent Application No. 2016-115040, filed Jun. 9, 2016.

TECHNICAL FIELD

The present invention relates to a method for preparing 4-(piperidin-4-yl)morpholine. According to the present invention, it is possible to provide a preparation method which is simple and provides 4-(piperidin-4-yl) morpholine with both a high yield and purity.

BACKGROUND ART 4-(piperidin-4-yl)morpholine is an important compound as a raw material or an intermediate of pharmaceutical products.

As a method for preparing 4-(piperidin-4-yl)morpholine, a preparation method in which 1-benzyl-4-piperidone is reacted with morpholine in a solvent to obtain 4-(1-benzylpiperidin-4-yl)morpholine, and 4-(piperidin-4-yl)morpholine is obtained from the resulting 4-(1-benzylpiperidin-4-yl)morpholine, is disclosed in Examples 6 and 7 of Patent literatures 1 and 2.

CITATION LIST

Patent Literature

[Patent literature 1] Japanese Translation Publication (Kohyo) No. 2010-535838
[Patent literature 2] Japanese Translation Publication (Kohyo) No. 2010-501517
[Patent literature 3] Japanese Examined Patent Publication (Kokoku) No. 7-116145
[Patent literature 4] Japanese Examined Patent Publication (Kokoku) No. 7-116146

SUMMARY OF INVENTION

Technical Problem

However, in the preparation method in Patent literatures 1 and 2, enamination and reduction are carried out as separate steps, and it is necessary to carry out the enamination reaction while removing water. Thus, the operation is complicated and time consuming.

Therefore, the object of the present invention is to provide a method for preparing 4-(piperidin-4-yl)morpholine, which is easy to operate.

Solution to Problem

The present inventors have conducted intensive studies into a method for preparing 4-(piperidin-4-yl)morpholine, which is easy to operate, and surprisingly found that 4-(1-benzylpiperidin-4-yl)morpholine can be prepared easily and in a short time, by carrying out enamination and reduction reaction simultaneously under specific conditions. That is, the present inventor found that 4-(piperidin-4-yl)morpholine could be obtained easily by conducting reductive amination in one pot under specific conditions.

The present invention is based on the above findings.
Namely, the present invention relates to:
[1] a method for preparing 4-(1-benzylpiperidin-4-yl)morpholine of the formula (3):

[Chem. 3]

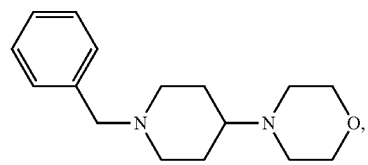

(3)

characterized in that 5-fold molar or more of morpholine of the formula (2):

[Chem. 2]

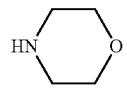

(2)

is added to 1-benzyl-4-piperidone of the formula (1):

[Chem. 1]

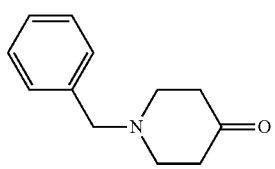

(1)

and the mixture is reacted with hydrogen under 1 MPa or less in the presence of a platinum catalyst or a palladium catalyst,
[2] the method for preparing 4-(1-benzylpiperidin-4-yl)morpholine of the item [1], wherein the platinum catalyst or palladium catalyst is a catalyst in which metal or compound of platinum or palladium is supported on a carrier,
[3] the method for preparing 4-(1-benzylpiperidin-4-yl)morpholine of the item [1] or [2], wherein the platinum catalyst or palladium catalyst is platinum/carbon catalyst, platinum/alumina catalyst, palladium/carbon catalyst, palladium/alumina catalyst, or palladium hydroxide/carbon catalyst,
[4] a method for preparing 4-(piperidin-4-yl)morpholine, comprising the steps of (1) removing morpholine from a mixed solution containing 4-(1-benzylpiperidin-4-yl)morpholine and unreacted morpholine, obtained by the method of item [1] or [2], and (2) debenzylating by reacting 4-(1-benzylpiperidin-4-yl)morpholine in which morpholine is removed, in the presence of hydrogen and palladium catalyst, to obtain 4-(piperidin-4-yl)morpholine of the formula (4):

[Chem. 4]

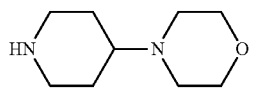

(4)

[5] the method for preparing 4-(piperidin-4-yl)morpholine of the item [4], further comprising a step of
(3) isolating 4-(piperidin-4-yl)morpholine obtained in the debenzylating step (2), by a distillation or recrystallization, and
[6] the method for preparing 4-(piperidin-4-yl)morpholine according to claim 4 or 5, the removal of morpholine in the removing step (1) is an evaporation, a solvent substitution, a crystallization, or a distillation.

Patent literatures 3 and 4 disclose a method for preparing 4-piperidinopiperidine(s) by performing reductive amination using 1-benzyl-4-piperidone and piperidine(s). However, in this method which is different from the present invention, morpholine is not used, and the conditions are not mild, and further side reactions may occur.

Advantageous Effects of Invention

According to the method for preparing 4-(piperidin-4-yl) morpholine of the present invention, 4-(1-benzylpiperidin-4-yl)morpholine can be easily obtained because the method is a reductive amination reaction simultaneously performing enamination and reduction reaction. Generally, for the reasons such as avoiding direct reduction of raw materials, a special reagent such as NaBH3(CN) or NaBH(OAc)3 is used as the reduction reagent used in the reductive amination. Therefore, it is not an industrially advantageous method, and especially the former is toxic and requires attention to use. Since hydrogen is used as a reducing agent in the method for preparing 4-(1-benzylpiperidin-4-yl)morpholine of the present invention, a post-treatment is easy as compared with the reaction using the reducing reagent. Further, the reductive amination is carried out under mild conditions using a platinum catalyst or a palladium catalyst (particularly a platinum catalyst) in the method for preparing 4-(1-benzylpiperidin-4-yl)morpholine of the present invention, and therefore production of by-products or impurities is suppressed, and 4-(1-benzylpiperidin-4-yl)morpholine can be prepared with both a high yield and purity.

In addition, since in a method for preparing 4-(piperidin-4-yl)morpholine of the present invention, the method for preparing 4-(1-benzylpiperidin-4-yl)morpholine of the present invention is used, the same effect can be obtained. Further, it is possible to carry out debenzylation efficiently by removing unreacted morpholine from the mixture product obtained by the method for preparing 4-(1-benzylpiperidin-4-yl)morpholine. Thus, according to the method for preparing 4-(piperidin-4-yl)morpholine of the present invention, 4-(piperidin-4-yl)morpholine can be produced with both a high yield and purity The catalyst used in reductive amination and debenzylation can be used in either a water-impregnated form or a dried form to remove moisture.

DESCRIPTION OF EMBODIMENTS

[1] Method for Preparing 4-(1-benzylpiperidin-4-yl)morpholine

In the method for preparing 4-(1-benzylpiperidin-4-yl) morpholine (hereinafter sometimes referred to as BMOPN preparation method), 5-fold molar or more of morpholine is added to 1-benzyl-4-piperidone and the mixture is reacted with hydrogen under 1 MPa or less in the presence of platinum catalyst or palladium catalyst.

1-benzyl-4-piperidone 1-benzyl-4-piperidone used as a raw material in the BMOPN preparation method of the present invention is a compound of the following formula (1) (hereinafter sometimes referred to as compound (1)).

[Chem. 5]

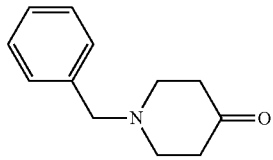

(1)

«Morpholine»

Morpholine used in the BMOPN preparation method of the present invention is a compound of the following formula (2) (hereinafter sometimes referred to as compound (2)).

[Chem. 6]

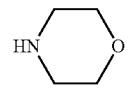

(2)

It is a heterocyclic amine and is a colorless liquid with amine odor at ordinary temperature. It is highly water soluble and sometimes used as a partial structure of medicine.

4-(1-benzylpiperidin-4-yl)morpholine 4-(1-benzylpiperidin-4-yl)morpholine obtained by the BMOPN preparation method of the present invention is a compound of the following formula (3) (hereinafter sometimes referred to as compound (3).

[Chem. 7]

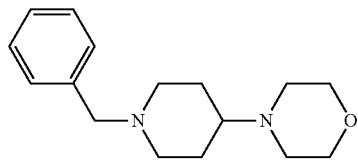

(3)

«Reductive Amination»

The reaction used in the BMOPN preparation method of the present invention is a reductive amination reaction in which enamine formation and reduction are simultaneously conducted. That is, the enamination is conducted by reacting the compound (1) with morpholine to obtain 4-(1-Benzyl-1,2,3,6-tetrahydropyridin-4-yl) morpholine. Concurrently, the resulting 4-(1-benzyl-1,2,3,6-tetrahydropyridin-4-yl) morpholine is reduced with hydrogen to obtain the compound (3). In the present invention, hydrogen is used as a reducing agent in order to perform the enamination and the reduction concurrently.

In the BMOPN preparation method of the present invention, the morpholine is contained in an amount of 5-fold molar or more with respect to the compound (1), preferably 5.5-fold molar or more, more preferably 6-fold molar or more, and most preferably 6.5-fold molar or more. That is, in the BMOPN preparation method of the present invention, morpholine is used as an amine for enamination and is used as a solvent for the compound (1). Using 5-fold molar or more of morpholine can accelerate the enamination. A by-production of 1-benzyl-4-hydroxypiperidine can be suppressed by using morpholine in the above-mentioned range.

Therefore, in the reductive amination reaction of the BMOPN preparation method of the present invention, it is preferable not to substantially contain a solvent other than the compound (1) and morpholine. However, it is not excluded to contain a solvent other than compound (1) and morpholine, as long as the effect of the present invention can be obtained.

(Hydrogen Gas)

In the BMOPN preparation method of the present invention, the reduction is conducted using hydrogen gas. The operation after completion of the reaction is only to remove the catalyst by filtration, and thus it does not require complicated operations to remove reagents performed in the case of using the reducing reagent. Therefore, the use of hydrogen gas is advantageous in the subsequent processing of the BMOPN preparation method of the present invention.

(Platinum or Palladium Catalyst)

In the BMOPN preparation method of the present invention, platinum or palladium catalyst is used as a catalyst.

The platinum catalyst is not particularly limited, as long as the effect of the present invention can be obtained, but is preferably a platinum/carbon catalyst or a platinum/alumina catalyst.

The palladium catalyst is not particularly limited, as long as the effect of the present invention can be obtained, but it is preferably a palladium/carbon catalyst, a palladium/alumina catalyst, or a palladium hydroxide/carbon catalyst.

In the reductive amination containing morpholine in an amount of 5-fold molar or more with respect to the compound (1), there is a possibility of poisoning of the catalyst by morpholine. However, it is possible to complete the reductive amination reaction by using the platinum catalyst or the palladium catalyst, as shown in Examples. The reductive amination reaction can be carried out under comparatively mild conditions (low temperature and low pressure) by using the platinum catalyst or the palladium catalyst, and therefore, the production of by-products or impurities can be suppressed.

In particular, it is possible to obtain the compound (3) with less impurities and high reaction selectivity, by using the platinum catalyst. Specifically, the platinum catalyst can suppress debenzylation of the compound (1). In addition, it makes enamine reduction proceed smoothly, and it is possible to suppress production of impurities derived from enamine.

In the case of using the palladium catalyst, a small amount of impurities which are not produced in the case of using the platinum catalyst, is produced as compared with the platinum catalyst. However, it promotes the reductive amination reaction and can suppress the production of many by-products or impurities, like the platinum catalyst.

Furthermore, in the case of using the palladium catalyst, the debenzylation reaction proceeds and some 4-(piperidin-4-yl)morpholine is produced. 4-(piperidin-4-yl)morpholine is an impurity in the BMOPN preparation method. However, 4-(piperidin-4-yl) morpholine is the final product when conducting the method for preparing 4-(piperidin-4-yl)morpholine described below after the BMOPN preparation method, and thus there is little effect on the method for preparing 4-(piperidin-4-yl)morpholine, even when 4-(piperidin-4-yl)morpholine is present.

The additive amount of the platinum catalyst or the palladium catalyst in the reductive amination reaction is not particularly limited. However, they can be exerted sufficient catalytic function, by adding 0.05 to 0.2% by weight in terms of platinum or palladium to the compound (1).

The pressure in the reductive amination of the BMOPN preparation method of the present invention is 1.0 MPa or less, preferably 0.95 MPa or less, more preferably 0.9 MPa or less, further preferably 0.8 MPa or less. When the pressure is 1.0 MPa or less, the reductive amination can be carried out under mild conditions, and thus the production of by-products or impurities can be suppressed. The lower limit of the pressure is not particularly limited, but, for example, is 0.1 MPa or more.

A temperature in the reductive amination of the BMOPN preparation method of the present invention is not particularly limited, as long as the effect of the present invention can be obtained, but is, for example, 20 to 150° C., preferably 60 to 100° C., more preferably 80 to 100° C.

Further, a time of the reductive amination is not particularly limited, as long as the reaction can be completed, but it is, for example, 1 to 20 hours, preferably 2 to 10 hours.

The reaction can be completed under comparatively mild conditions by conducting the reductive amination in the above ranges of temperature and time. In addition, pressure, reaction temperature, and reaction time can be appropriately combined by a person skilled in the art so that the reductive amination is completed. That is, when the pressure is high or reaction temperature is high, the reaction time for reductive amination tends to be shortened. On the contrary, when the pressure is low or the reaction temperature is low, the reaction time tends to be long.

Accordingly, those skilled in the art can combine pressure, reaction temperature, and reaction time to set the conditions under which the reductive amination reaction may be completed.

[2] Method for Preparing 4-(piperidin-4-yl)morpholine

The method for preparing 4-(piperidin-4-yl)morpholine of the present invention (hereinafter sometimes referred to as 4-MOPN preparation method) comprises steps of (1) removing morpholine from a mixed solution containing the compound (3) obtained by the method for preparing the compound (3) and unreacted morpholine, by an evaporation, a solvent substitution, a crystallization, or a distillation; and (2) debenzylating by reacting the compound (3) in which morpholine is removed, in the presence of hydrogen and catalyst, to obtain 4-(piperidin-4-yl)morpholine.

4-(piperidin-4-yl)morpholine 4-(piperidin-4-yl)morpholine obtained in the 4-MOPN preparation method of the present invention is a compound of the following formula (4) (hereinafter sometimes referred to as compound (4)).

[Chem. 8]

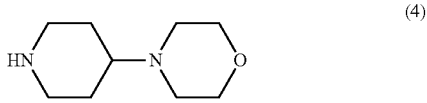 [SMILES: C1CC(N2CCOCC2)CCN1]

«Morpholine Removal Step (1)»

In the morpholine removal step (1), the unreacted morpholine is removed by evaporation, solvent substitution, crystallization, or distillation from the mixed solution containing unreacted morpholine and the compound (3) obtained by adding morpholine in an amount of 5-fold molar or more with respect to the compound (1), reacting under a hydrogen gas of 1 MPa or less by using a platinum catalyst or a palladium catalyst, and filtering the catalyst. In the debenzylation step to be described later, if the reaction mixture contains a large amount of morpholine, the progress of the debenzylation reaction is suppressed. Therefore, the debenzylation reaction can be accelerated by removing morpholine from the mixed solution containing the compound (3) and morpholine.

The method for removing morpholine includes, but is not limited to, an evaporation, a solvent substitution, a crystallization, or a distillation. The evaporation is a method of evaporating and removing morpholine by heating under normal pressure or under reduced pressure at room temperature or under heating. For example, the compound (3) can be concentrated by evaporating morpholine using a rotary evaporator.

In the method of solvent substitution, a predetermined amount of morpholine is evaporated and removed by heating under normal pressure or under reduced pressure at room temperature or under heating, and then a 2nd solvent (for example, a solvent to be used in the next step) is added and the same procedure is repeated. Morpholine can be efficiently removed and replaced with a second solvent by such the treatment.

In the crystallization method, the compound (3) is crystallized. For example, the compound (3) can be crystallized and separated from morpholine by adding an appropriate solvent to the mixed solution or the reaction mixture in which the amount of morpholine is reduced by the evaporation.

Distillation is a method of separating and purifying compound (3) from the reaction mixture containing morpholine by heating under reduced pressure or normal pressure.

The amount of morpholine remaining is preferably as small as possible. According to the method for removing morpholine by crystallization, the remaining amount of morpholine is theoretically 0%. The remaining amount of morpholine can be reduced to almost 0% even when removed by evaporation, solvent substitution, or distillation. However, even if morpholine remains in the reaction mixture, the debenzylation reaction can be conducted sufficiently. The allowable residual amount of morpholine, for 1 part by weight of the compound (3), is preferably 1 part by weight or less, more preferably 0.5 parts by weight or less, even more preferably 0.3 parts by weight or less, most preferably 0.1 parts by weight or less. The less remaining amount of morpholine can accelerate debenzylation reaction.

«Debenzylation Step (2)»

In the debenzylation step (2) of the 4-MOPN preparation method of the present invention, the compound (3) from which morpholine has been removed is reacted in the presence of hydrogen and a catalyst to obtain a compound (4).

In the debenzylation step (2) of the present invention, the debenzylation reaction is carried out in the presence of hydrogen gas. The catalyst to be used is not particularly limited, but there may be mentioned palladium catalyst.

The palladium catalyst is not particularly limited, as long as the effect of the present invention can be obtained. However, preferably there may be mentioned a palladium/carbon catalyst.

The additive amount of the catalyst in the debenzylation reaction is not particularly limited. However, it can be exerted sufficient catalytic function, by adding 0.3 to 1.5% by weight in terms of palladium to the compound (3).

The pressure in the debenzylation reaction is not particularly limited, as long as the effect of the present invention can be obtained, but is, for example, 1.5 MPa or less, preferably 1.5 MPa or less, more preferably 1.2 MPa or less, even more preferably 1 MPa or less, most preferably 0.8 MPa or less. The lower limit of the pressure is not particularly limited, but, for example, is 0.1 MPa or more.

The temperature in the debenzylation reaction is not particularly limited, as long as the effect of the present invention can be obtained, but is, for example, 20 to 150° C., preferably 60 to 100° C., more preferably 80 to 100° C. It is possible to suppress the deactivation of the catalyst and suppress the production of impurities by reacting under comparatively mild conditions.

The time of the debenzylation reaction is not particularly limited, as long as the reaction can be completed, but it is, for example, 1 to 20 hours, preferably 2 to 10 hours.

The pressure, reaction temperature, and the reaction time in the debenzylation reaction can be appropriately combined by a person skilled in the art so that the debenzylation reaction is completed. The reaction can be completed under comparatively mild conditions by conducting the debenzylation in the above ranges of temperature and time. The pressure, reaction temperature, and reaction time can be appropriately combined by a person skilled in the art so that the debenzylation reaction is completed. That is, when the pressure is high or the reaction temperature is high, the reaction time for debenzylation tends to be shortened. On the contrary, when the pressure is low or the reaction temperature is low, the reaction time tends to be long.

Accordingly, those skilled in the art can combine pressure, reaction temperature, and reaction time to set the conditions under which the debenzylation reaction may be completed.

«Isolation Step (3)»

In the isolation step (3) of the 4-MOPN preparation method of the present invention, the compound (4) obtained in the debenzylation step (2) is isolated by distillation or recrystallization. In order to use the compound (4) as a pharmaceutical raw material or an intermediate, it is necessary to highly purify, and thus, it is preferable to purify by recrystallization or distillation.

The method of recrystallization is not particularly limited, but it can be recrystallized by using an appropriate solvent such as hydrocarbons, ethers, esters or the like.

With regard to the distillation purification, the distillation purification method usually used in the technical field to which the present invention belongs can be used without limitation.

EXAMPLES

The present invention will now be further illustrated by, but is by no means limited to, the following Examples.

Example 1

In this Example, the compound (1) was reductively aminated using a platinum/carbon catalyst.

The compound (1) (2.0 g; 11 mmol), morpholine (8.0 g; 91.8 mmol; 8.7-fold moles with respect to the compound (1)), and the platinum/carbon catalyst (2 mg in terms of metallic platinum) were placed in an autoclave with a capacity of 200 mL, and then the whole was stirred at 80° C., under a hydrogen pressure of 0.5 MPa for 8 hours. The reaction mixture was analyzed by gas chromatography. As a result, the residual amount of the raw material, i.e. compound (1) and the reaction intermediate, i.e. 4-(1-benzyl-1,2,3,6-tetrahydropyridin-4-yl) morpholine is reduced to 1% or less in total and the desired compound (3) was 93.6% (Table 1).

Example 2

In this Example, the compound (1) was reductively aminated using a palladium/alumina catalyst.

The reaction described in Example 1 was carried out for six hours except that the palladium/alumina catalyst (2 mg in terms of metallic palladium) was used instead of the platinum/carbon catalyst. The reaction mixture was analyzed by gas chromatography. As a result, a compound (4) in which objective compound (3) was further hydrogenated was also produced, but the compound (3) was selectively obtained by the reaction (Table 1).

Example 3

In this Example, the compound (1) was reductively aminated using a palladium/carbon catalyst.

The reaction described in Example 1 was carried out for two hours except that the palladium/carbon catalyst (2 mg in terms of metallic palladium) was used instead of the platinum/carbon catalyst. The reaction mixture was analyzed by gas chromatography. As a result, a compound (4) in which objective compound (3) was further hydrogenated was also produced, but the compound (3) was selectively obtained by the reaction (Table 1).

Example 4

In this Example, the compound (1) was reductively aminated using a palladium hydroxide/carbon catalyst.

The reaction described in Example 1 was carried out for four hours except that the palladium hydroxide/carbon catalyst (2 mg in terms of metallic palladium) was used instead of the platinum/carbon catalyst. The reaction mixture was analyzed by gas chromatography. As a result, a compound (4) in which objective compound (3) was further hydrogenated was also produced, but the compound (3) was selectively obtained by the reaction (Table 1).

Comparative Example 1

In this Comparative Example, the compound (1) was reductively aminated using the amount of less than 5-fold molar of morpholine.

The reaction described in Example 1 was carried out for four hours except that 2.0 g of morpholine and 6.0 g of 2-propanol instead of 8.0 g of morpholine. The reaction mixture was analyzed by gas chromatography. As a result, by-products of more than 10% were produced and the reaction selectivity was low (Table 1).

Comparative Example 2

In this Comparative Example, the compound (1) was reductively aminated using a Raney nickel catalyst.

The reaction described in Example 1 was carried out for eight hours except that the Raney nickel catalyst (1.0 g) was used instead of the platinum/carbon catalyst. The reaction mixture was analyzed by gas chromatography. As a result, a large amount of raw materials and reaction intermediates remained, and the reaction selectivity was also low (Table 1).

Comparative Example 3

In this Comparative Example, the compound (1) was reductively aminated using a rhodium/carbon catalyst.

The reaction described in Example 1 was carried out for eight hours except that the rhodium/carbon catalyst (2 mg in terms of metallic rhodium) was used instead of the platinum/carbon catalyst. The reaction mixture was analyzed by gas chromatography. As a result, a large amount of raw materials and reaction intermediates remained, and the reaction selectivity was also low (Table 1).

Comparative Example 4

In this Comparative Example, the compound (1) was reductively aminated using a ruthenium/carbon catalyst.

The reaction described in Example 1 was carried out for eight hours except that the ruthenium/carbon catalyst (2 mg in terms of metallic ruthenium) was used instead of the platinum/carbon catalyst. The reaction mixture was analyzed by gas chromatography. As a result, a large amount of raw materials and reaction intermediates remained, and the reaction selectivity was also low (Table 1).

The results of Examples 1 to 4, Comparative Examples 1 to 4, and the following Example 5 are summarized in Table 1.

TABLE 1

| | Gas chromatograph area percentage (excluding morpholine) | | | |
|---|---|---|---|---|
| Examples | Compound (3) | Compound (4) | Starting compound (1) and reaction intermediate | Direct reduced compound and other impurities |
| Example 1 | 93.6% | 0.0% | 0.5% | 5.8% |
| Example 2 | 91.8% | 6.3% | 0.8% | 1.3% |
| Example 3 | 80.3% | 15.5% | 0.0% | 4.2% |
| Example 4 | 77.5% | 19.7% | 1.0% | 1.9% |
| Example 5 | 94.3% | 0.0% | 0.2% | 5.5% |
| Comparative Example 1 | 88.7% | 0.2% | 0.2% | 11.0% |
| Comparative Example 2 | 8.4% | 0.0% | 58.8% | 32.9% |
| Comparative Example 3 | 50.7% | 2.9% | 33.9% | 12.5% |
| Comparative Example 4 | 6.9% | 0.1% | 29.9% | 63.1% |

Reaction intermediate: 4-(1-Benzyl-1,2,3,6-tetrahydropyridin-4-yl) morpholine
Direct reduced compound: 1-benzyl-4-hydroxypiperidine Example 5

In this Example, the compound (1) was reductively aminated using a platinum/carbon catalyst.

The compound (1) (0.30 kg; 1.6 mol), morpholine (1.2 kg), and the platinum/carbon catalyst (0.72 g in terms of metallic platinum) were placed in an autoclave with a capacity of 3 L, and then the whole was stirred at 80° C., under a hydrogen pressure of 0.5 MPa for 7 hours. After cooling the reaction, the catalyst was filtered and washed with morpholine to obtain a filtrate. The resulting filtrate was analyzed by gas chromatography. As a result, the yield of the compound (3) analyzed by the internal standard method was 92%. The compound (3) was 94.3% and the 1-benzyl-4-hydroxypiperidine was 4.4% in the area percentage excluding morpholine (Table 1).

Example 6

In this Example, morpholine was distilled away from a mixture of the compound (3) and morpholine, followed by a debenzylation reaction to obtain a compound (4).

Morpholine was distilled away under reduced pressure from 15 g of the reaction filtrate containing 3.0 g (12 mmol) of the compound (3) obtained in the same manner as in Example 5, to obtain 3.7 g of concentrated residue. The remaining amount of morpholine in the resulting concentrated residue was 0.1 parts by weight with respect to 1 part by weight of the compound (3). The total amount of resulting concentrated residue, 2-propanol (6.9 g), and the palladium/carbon catalyst (7.5 mg in terms of metallic palladium) were placed in an autoclave with a capacity of 200 mL, and then the whole was stirred at 80° C., under a hydrogen pressure of 0.5 MPa for 4 hours. The reaction mixture was analyzed by gas chromatography. As a result, the compound (4) was 98.8%, and the raw material compound (3) was 0.1% in area percentage excluding the compounds with low boiling points (Table 2).

Example 7

In this Example, morpholine was distilled away, followed by a debenzylation reaction to obtain a compound (4).

Morpholine was distilled away under reduced pressure from 15 g of the reaction filtrate containing 3.0 g (12 mmol) of the compound (3) obtained in the same manner as in Example 5, to obtain 6.5 g of concentrated residue. The remaining amount of morpholine in the concentrated residue was 1.0 part by weight with respect to 1 part by weight of the compound (3). The reaction was carried out in the same manner as in Example 6, using the concentrated residue (Table 2).

Example 8

In this Example, morpholine was removed by solvent substitution, and then the compound (4) was obtained by a debenzylation reaction.

Morpholine was distilled away under reduced pressure from 15 g of the reaction filtrate containing 3.0 g (12 mmol) of the compound (3) obtained in the same manner as in Example 5, and the filtrate was concentrated to 3.8 g. Then, 4.5 g of 2-propanol was added thereto, and morpholine and 2-propanol were distilled away under reduced pressure, to obtain 3.5 g of concentrated residue. The remaining amount of morpholine in the concentrated residue was 0.02 parts by weight with respect to 1 part by weight of the compound (3). The reaction was carried out in the same manner as in Example 6, using the concentrated residue (Table 2).

Example 9

In this Example, morpholine was removed by distillation purification, and then the compound (4) was obtained by a debenzylation reaction.

203 g of the reaction filtrate containing 40 g (0.15 mol) of the compound (3) obtained by the same method as in Example 5 was purified by distillation (column top temperature 162 to 170° C./0.7 mmHg), to obtain 17.9 g of compound (3). As a result of analyzing by gas chromatography, the area percentage of the compound (3) was 98.3% and the area percentage of morpholine was 0.0%. When the fractions before and after this fraction were combined, the recovery rate by distillation was 96%. The reaction was carried out in the same manner as in Example 6, using 3.0 g of the resulting compound (3) (Table 2).

Example 10

In this Example, morpholine was removed by recrystallization, and then the compound (4) was obtained by a debenzylation reaction.

100 g of the reaction filtrate containing 20 g (76 mmol) of the compound (3) obtained in the same manner as in Example 5 was recrystallized with methylcyclohexane, to obtain 12 g of the compound (3) (recovery rate of 63%). As a result of analysis by gas chromatography, the area percentage of the compound (3) was 99.8% and morpholine was not detected. The reaction was carried out in the same manner as in Example 6, using 3.0 g of the resulting compound (3) (Table 2).

Comparative Example 5

In this Comparative Example, the debenzylation reaction was carried out without removing morpholine.

15 g of the reaction filtrate containing 3.0 g (12 mmol) of the compound (3) obtained in the same manner as in Example 5, and a palladium/carbon catalyst (7.5 mg in terms of metallic palladium) were placed in an autoclave with a capacity of 200 mL, and then the whole was stirred at 80° C., under a hydrogen pressure of 0.5 MPa for 6 hours. After cooling the reaction, the catalyst was filtered, to obtain a filtrate. The resulting filtrate was analyzed by gas chromatography. As a result, the area percentage (excluding the compounds with low boiling points) of the compound (4) was 82.5%, and the compound (3) of 16.4% area percentage (excluding the compounds with low boiling points) remained (Table 2).

The results of the above Examples 6 to 10, Comparative Example 5, and the following Example 11 are summarized in Table 2.

TABLE 2

| Examples | Gas chromatograph area percentage (excluding compounds with low boiling points) | |
|---|---|---|
| | Compound (4) | Compound (3) |
| Example 6 | 98.8% | 0.1% |
| Example 7 | 98.5% | 0.6% |
| Example 8 | 98.7% | 0.0% |
| Example 9 | 99.0% | 0.1% |
| Example 10 | 99.8% | Not detected |
| Example 11 | 100.0% | Not detected |
| Comparative Example 5 | 82.5% | 16.4% |

As shown in Table 2, in the compound (4) obtained in Examples 6 to 11, the debenzylation reaction sufficiently proceeded and an efficient reaction was obtained. On the other hand, in Comparative Example 5, the compound (3) remained, and the debenzylation reaction was incomplete.

Example 11

The compound (3) (120 g; 0.46 mol), 2-propanol (276 g), and the palladium/carbon catalyst (0.3 g in terms of metallic palladium) were placed in an autoclave with a capacity of 1 L, and then the whole was stirred at 80° C., under a hydrogen pressure of 0.5 MPa for 7 hours. After cooling the reaction, the catalyst was filtered and washed with 2-propanol to obtain a filtrate. The resulting filtrate was analyzed by gas chromatography. As a result, the yield of the compound (4) analyzed by the internal standard method was 97%, and the area percentage (excluding the solvent and the compounds with low boiling points) of the compound (4) was 100% (Table 2).

Example 12

In this Example, the compound (4) was isolated by recrystallization using methylcyclohexane.

The reaction mixture containing 10 g of the compound (4) obtained in the same manner as in Example 11 was recrystallized using methylcyclohexane, to obtain 6.2 g of the compound (4) as a crystal. The recovery rate of the resulting compound (4) was 62.5%. As a result of analysis by gas chromatography, the area percentage of the compound (4) was 99.5%.

Example 13

In this Example, compound (4) was isolated by recrystallization using dibutyl ether.

The reaction mixture containing 4.7 g of the compound (4) obtained by the same method as in Example 11 was recrystallized with dibutyl ether, to obtain 1.6 g of the compound (4). As a result of analysis by gas chromatography, the area percentage of the compound (4) was 100.0%. The recovery ratio of the resulting compound (4) was 35.0%

Example 14

In this Example, compound (4) was isolated by distillation purification.

The reaction mixture containing 38 g of the compound (4) obtained by the same manner as in Example 11 was purified by distillation (column top temperature 91 to 93° C./0.9 mmHg), to obtain 17 g of Compound (4). As a result of analyzing by gas chromatography, the area percentage of the compound (4) was 99.9%. When the fractions before and after this fraction were combined, the recovery rate was 93.9%.

INDUSTRIAL APPLICABILITY 4-(1-benzylpiperidin-4-yl)morpholine and 4-(piperidin-4-yl)morpholine obtained by the preparation method of the present invention can be usefully used as raw materials or intermediates of pharmaceuticals or the like.

Although the present invention has been described with reference to specific embodiments, various changes and modifications obvious to those skilled in the art are possible without departing from the scope of the appended claims.

The invention claimed is:

1. A method for preparing 4-(1-benzylpiperidin-4-yl)morpholine of the formula (3):

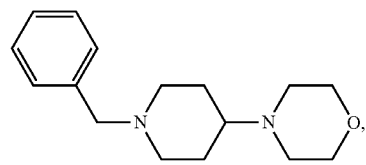
(3)

characterized in that 5-fold molar or more of morpholine of the formula (2):

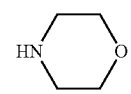
(2)

is added to 1-benzyl-4-piperidone of the formula (1):

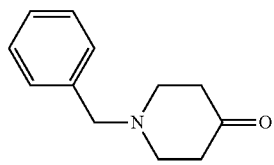
(1)

and the mixture is reacted with hydrogen under 1 MPa or less in the presence of a platinum catalyst or a palladium catalyst.

2. The method for preparing 4-(1-benzylpiperidin-4-yl)morpholine according to claim 1, wherein the platinum catalyst or palladium catalyst is a catalyst in which metal or compound of platinum or palladium is supported on a carrier.

3. The method for preparing 4-(1-benzylpiperidin-4-yl)morpholine according to claim 1, wherein the platinum catalyst or palladium catalyst is platinum/carbon catalyst, platinum/alumina catalyst, palladium/carbon catalyst, palladium/alumina catalyst, or palladium hydroxide/carbon catalyst.

4. A method for preparing 4-(piperidin-4-yl)morpholine, comprising the steps of
(1) removing morpholine from a mixed solution containing 4-(1-benzylpiperidin-4-yl)morpholine and unreacted morpholine, obtained by the method according to claim 1, and
(2) debenzylating by reacting 4-(1-benzylpiperidin-4-yl)morpholine in which morpholine is removed, in the presence of hydrogen and palladium catalyst, to obtain 4-(piperidin-4-yl)morpholine of the formula (4):

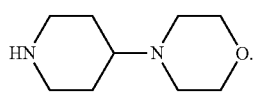
(4)

5. The method for preparing 4-(piperidin-4-yl)morpholine according to claim 4, further comprising a step of
(3) isolating 4-(piperidin-4-yl)morpholine obtained in the debenzylating step (2), by a distillation or recrystallization.

6. The method for preparing 4-(piperidin-4-yl)morpholine according to claim 4, wherein the removal of morpholine in the removing step (1) is an evaporation, a solvent substitution, a crystallization, or a distillation.

7. The method for preparing 4-(1-benzylpiperidin-4-yl) morpholine according to claim 2, wherein the platinum catalyst or palladium catalyst is platinum/carbon catalyst, platinum/alumina catalyst, palladium/carbon catalyst, palladium/alumina catalyst, or palladium hydroxide/carbon catalyst.

8. A method for preparing 4-(piperidin-4-yl)morpholine, comprising the steps of
   (1) removing morpholine from a mixed solution containing 4-(1-benzylpiperidin-4-yl)morpholine and unreacted morpholine, obtained by the method according to claim 2, and
   (2) debenzylating by reacting 4-(1-benzylpiperidin-4-yl)morpholine in which morpholine is removed, in the presence of hydrogen and palladium catalyst, to obtain 4-(piperidin-4-yl)morpholine of the formula (4):

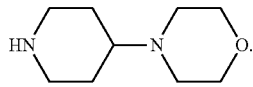

(4)

9. The method for preparing 4-(piperidin-4-yl)morpholine according to claim 5, wherein the removal of morpholine in the removing step (1) is an evaporation, a solvent substitution, a crystallization, or a distillation.

* * * * *